United States Patent
Haluska et al.

(10) Patent No.: US 6,755,963 B2
(45) Date of Patent: Jun. 29, 2004

(54) HYDROGENATION PROCESS FOR HYDROCARBON RESINS

(75) Inventors: Jerry L. Haluska, Baton Rouge, LA (US); Kenneth Lloyd Riley, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/261,773

(22) Filed: Oct. 1, 2002

(65) Prior Publication Data

US 2003/0150778 A1 Aug. 14, 2003

Related U.S. Application Data

(63) Continuation of application No. 09/483,068, filed on Jan. 14, 2000, now abandoned, which is a continuation-in-part of application No. 09/231,156, filed on Jan. 15, 1999, now Pat. No. 6,162,350, which is a continuation-in-part of application No. 08/900,389, filed on Jul. 15, 1997, now Pat. No. 6,156,695.

(51) Int. Cl.$^7$ .................. C10G 45/00; C10G 45/04; B01J 23/00; C08F 240/00; C08F 6/00
(52) U.S. Cl. .................. 208/143; 208/216 PP; 208/251 H; 208/254 H; 502/305; 502/313; 502/325; 528/483; 528/485; 528/487; 528/490; 525/327.9; 525/331.9
(58) Field of Search .................. 208/143, 216 PP, 208/251 H, 254 H; 502/305, 313, 325; 528/423, 485, 487, 490, 483; 525/327.9, 331.9

(56) References Cited

U.S. PATENT DOCUMENTS

| | | | | | |
|---|---|---|---|---|---|
| 4,102,822 | A | * | 7/1978 | Mulaskey | 252/465 |
| 4,384,080 | A | * | 5/1983 | Matsubara et al. | 525/338 |
| 4,395,328 | A | * | 7/1983 | Hensley, Jr. et al. | 208/251 H |
| 4,533,700 | A | * | 8/1985 | Mizui et al. | 525/285 |
| 5,268,399 | A | * | 12/1993 | Wouters et al. | 523/336 |
| 5,820,749 | A | * | 10/1998 | Haluska et al. | 208/216 PP |
| 6,156,695 | A | * | 12/2000 | Soled et al. | 502/305 |
| 6,162,350 | A | * | 12/2000 | Soled et al. | 208/113 |

* cited by examiner

*Primary Examiner*—Mark L. Bell
*Assistant Examiner*—Patricia L. Hailey
(74) *Attorney, Agent, or Firm*—William B. Muller; Leandro Arechederra

(57) ABSTRACT

This invention provides a process for hydrotreating hydrocarbon resins, which process comprises contacting a feedstock comprising a hydrocarbon resin or rosin, under suitable hydrotreating conditions, with a bulk multimetallic catalyst comprised of at least one Group VIII non-noble metal and at least two Group VIB metals and wherein the ratio of Group VIB metal to Group VIII non-noble metal is from about 10:1 to about 1:10. The process according to the invention can achieve increased hydrocarbon resin productivity through increase in throughput volumes and effective catalyst lifetimes. The process of the invention is desirably practiced with a bulk catalyst consisting of only the combination of the metal species with the active metal components. The absence of carrier substrates largely removes the possibility of halogen accumulation on substrate surfaces that, in turn, can acidify metal catalysts such that additional, progressive cracking of the hydrocarbon resin molecules occurs.

18 Claims, No Drawings

HYDROGENATION PROCESS FOR HYDROCARBON RESINS

RELATED APPLICATIONS

This application is a continuation of U.S. application Ser. No. 09/483,068, filed Jan. 14, 2000, now abandoned, which is a continuation-in-part of U.S. application 09/231,156 filed Jan. 15, 1999, now U.S. Pat. No. 6,162,350, which is a continuation-in-part of U.S. application Ser. No. 08/900,389 flied Jul. 15, 1997, now U.S. Pat. No. 6,156,695.

TECHNICAL FIELD

This invention relates to a catalytic hydrotreating process useful for hydrocarbon resin and rosin feeds. In particular the invention relates to an improved process for hydrotreating such resins and rosins with hydrogenation metal catalyst compounds having sulfided nickel molybdotungstate catalysts.

BACKGROUND OF THE INVENTION

Hydrotreating processes for the hydrogenation, desulfurization and denitrogenation of hydrocarbon compounds including such compositions of matter as petroleum fuels, white oils, lubricating oil additives and hydrocarbon resins are well known and practiced industrially. In particular, it is known that heterogeneous catalyst systems, those supported on metal oxide supports, can be advantageously used to facilitate this process. Effective reaction rates require that hydrogen gas molecules and the hydrocarbon compounds come into contact with each other in the presence of an active metal catalyst, and those active metal catalysts are typically affixed within the pores of inert supports. It is generally believed that if the pores are of insufficient design the large hydrocarbon molecules are so restricted in movement into, through and out of the pores that reaction rates are diminished. Accordingly there is a large body of knowledge relating to hydrotreating hydrocarbon compounds with heterogeneous catalysts, see for example the description of U.S. Pat. No. 5,820,749, and documents cited therein. A preferred process of the invention uses a catalyst comprising the metals nickel and/or cobalt and one or both of molybdenum and tungsten on the inert support of that invention.

A nickel molybdotungstate catalyst is disclosed in WO 99/03578. The catalyst is prepared by decomposing a nickel (ammonium) molybdotungstate precursor and sulfiding, either pre-use or in situ, the decomposition product. Suggested uses for the catalyst include desulfurization and denitrogenation.

As is apparent from this document, and those it discusses, increased productivity and run times without catalyst degradation is desirable, particularly for hydrocarbon resins, if color, aromaticity, and softening point characteristics can be retained or improved.

SUMMARY OF INVENTION/INVENTION DISCLOSURE

In accordance with this invention there is provided a process for hydrotreating hydrocarbon resins, which process comprises contacting a feedstock comprising a hydrocarbon resin or rosin, under suitable hydrotreating conditions, with a bulk multimetallic catalyst comprised of at least one Group VIII non-noble metal and at least two Group VIB metals and wherein the ratio of Group VIB metal to Group VIII non-noble metal is from about 10:1 to about 1:10. The process according to the invention can achieve increased hydrocarbon resin productivity through increase in throughput volumes and effective catalyst lifetimes.

Hydrocarbon resins prepared from catalytically or thermally polymerized feedstreams and hydrogenated according to the invention exhibit color, aromaticity and softening point characteristics at least equivalent to previously available hydrogenated resins. The process of the invention is desirably practiced with a bulk catalyst consisting of only the combination of the metal species with the active metal components. It is thus usable in fixed bed hydrogenation reactor while avoiding the negative aspects of inert substrate carriers for supporting the catalytically active metal compounds. The absence of carrier substrates largely removes the possibility of halogen accumulation on substrate surfaces that, in turn, can acidify metal catalysts such that additional, progressive cracking of the hydrocarbon resin molecules occurs. This cracking deteriorates important physical properties such as resin softening point, decreases product yields, and reduces effective catalyst life.

BEST MODE AND EXAMPLES OF THE INVENTION

A preferred process according to the invention comprises the step of hydrogenating or hydrotreating (used interchangeably herein) a catalytically or thermally prepared hydrocarbon resin in the presence of the above described catalyst. Any of the known processes for catalytically hydrogenating hydrocarbon resins can be modified in accordance with the invention by substituting the catalyst system of the invention, in particular the processes of U.S. Pat. Nos. 5,171,793, 4,629,766 and 4,328,090 and WO 95/12623 are suitable. Each is referred to and incorporated by reference for purposes of U.S. patent practice, and is referred to for description of polymerization processes, monomer selection, hydrogenation processes, and end use applications of the described resins.

Other patent literature describes suitable processes for modification in accordance with the invention. For example, EP 0 082 726 describes a process for the hydrogenation of petroleum resins from catalytic or thermal polymerization of olefin and diolefin containing streams, using nickel-tungsten catalyst on a gamma-alumina support wherein the hydrogen pressure is $1.47 \times 10^7 - 1.96 \times 10^7$ Pa and the temperature is in the range of 250–330° C. The feedstreams are said to contain $C_5$ and/or $C_6$ olefin and/or diolefin streams, and, for catalytic polymerization, $C_8/C_9$ aromatic olefins, e.g., styrene, vinyl benzene and optionally indene. Thermal polymerization is usually done at 160 to 320° C., at a pressure of $9.8 \times 10^5$ to $11.7 \times 10^5$ Pa and for a period typically of 1.5 to 4 hours. After hydrogenation the reactor mixture may be flashed and further separated to recover the hydrogenated resin. Steam distillation may be used to eliminate oligomers, preferably without exceeding 325° C. resin temperature.

Additional description and information appears in the technical literature. The term hydrocarbon resin as used in the specification and claims include the known low molecular weight polymers derived from cracked petroleum distillates, coal tar, turpentine fractions and a variety of pure monomers. The number average molecular weight is usually below 2000, and physical forms range from viscous liquids to hard, brittle solids. Polymerization feedstreams are derived from the sources described above via various known means and methods of fractionation. Friedel-Crafts polymerization is generally accomplished by use of known Lewis acid catalysts in a polymerization solvent, and removal of solvent and catalyst by washing and distillation.

The invention hydrotreating process is particularly suitable for such Lewis acid catalyzed resins due to residual halogen containing reaction products from the polymerization process. Thermal catalytic polymerization is also utilized, particularly for aliphatic, cyclo-aliphatic and aliphatic-aromatic petroleum resins. The preferred hydrocarbon resins are those known to be useful as tackifiers for adhesive compositions, particularly the petroleum resins derived from the deep cracking of petroleum distillates, hydrocarbon resins from pure aromatic monomers, the coumarone-indene resins from coal tar and the polyterpenes derived from turpentine fractions. Included in petroleum resins are those that have been modified with aromatic or terpene containing feedstreams. For additional description of feedstream derivation, monomer composition, methods of polymerization and hydrogenation, reference may be made to patent literature (see Background) and to technical literature, e.g., Hydrocarbon Resins, Kirk-Othmer Encyclopedia of Chemical Technology, v. 13, pp. 717–743 (J. Wiley & Sons, 1995); Encycl. of Poly. Sci. and Eng'g., vol. 7, pp. 758–782 (J. Wiley & Sons, 1987), and the references cited in both of them. Additionally, reference may be made to EP 0 240 253 and its corresponding application U.S. Ser. No. 07/065,792, filed Jun. 27, 1987. All of these references are incorporated by reference for purposes of U.S. patent practice.

The known natural resins will additionally be suitable for hydrotreating in accordance with the invention. The natural resins are traditional materials documented in the literature, see for example, Encycl. of Poly. Sci. and Eng'g., vol. 14, pp. 438–452 (John Wiley & Sons, 1988).

The rosins capable of hydrotreating in accordance with the invention includes any of those known in the art to be suitable as tackifying agents, this specifically includes the esterified rosins. The principal sources of the rosins include gum rosins, wood rosin, and tall oil rosins which typically have been extracted or collected from their known sources and fractionated to varying degrees. Additional background can be obtained from technical literature, e.g., Kirk-Othmer Encycl. of Chem. Tech., vol. 17, pp. 475–478 (John Wiley & son, 1968) and *Handbook of Pressure-Sensitive Adhesive Technology*, ed. by D. Satas, pp. 353–356 (Van Nostrand Reinhold Co., 1982).

The hydroprocessing, hydrotreating or hydrogenation catalyst used in the practice of the present invention is a bulk multimetallic catalyst comprised of at least one Group VIII non-noble metal and at least one, preferably two, Group VIB metals and wherein the ratio of Group VIB metal to Group VIII non-noble metal is from about 10:1 to about 1:10. It is preferred that the catalyst be a bulk trimetallic catalyst comprised of one Group VIII non-noble metal, preferably Ni or Co and the two Group VIB metals Mo and W. It is preferred that the ratio of Mo to W be about 9:1 to about 1:9.

The preferred bulk trimetallic catalyst compositions used in the practice of the present invention is represented by the formula:

$$(X)_b(Mo)_c(W)_dO_z$$

wherein X is a Group VIII non-noble metal, the molar ratio of b: (c+d) is 0.5/1 to 3/1, preferably 0.75/1 to 1.5/1, more preferably 0.75/1 to 1.25/1;

The molar ratio of c:d is preferably >0.01/1, more preferably >0.1/1, still more preferably 1/10 to 10/1, still more preferably 1/3 to 3/1, most preferably substantially equimolar amounts of Mo and W, e.g., 2/3 to 3/2; and z=[2b+6 (c+d)]/2.

The essentially amorphous material has a unique X-ray diffraction pattern showing crystalline peaks at d=2.53 Angstroms and d=1.70 Angstroms.

The mixed metal oxide is readily produced by the decomposition of a precursor having the formula:

$$(NH_4)_a(X)_b(Mo)_c(W)_dO_z$$

wherein the molar ratio of a:b is $\leq 1.0/1$, preferably 0–1; and b, c, and d, are as defined above, and z=[a+2b+6 (c+d)]/2. The precursor has similar peaks at d=2.53 and 1.70 Angstroms.

Decomposition of the precursor may be effected at elevated temperatures, e.g., temperatures of at least about 300° C., preferably about 300–450° C., in a suitable atmosphere, e.g., inerts such as nitrogen, argon, or steam, until decomposition is substantially complete, i.e., the ammonium is substantially completely driven off. Substantially complete decomposition can be readily established by thermogravimetric analysis (TGA), i.e., flattening of the weight change curve.

The catalyst compositions used in the practice of the present invention can be prepared by any suitable means. One such means is a method wherein not all of the metals are in solution. Generally, the contacting of the metal components in the presence of the protic liquid comprises mixing the metal component and subsequently reacting the resulting mixture. It is essential to the solid route that at least one of the metal components is added at least partly in the solid state during the mixing step and that the metal of at least one of the metal components which have been added at least partly in the solid state, remains at least partly in the solid state during the mixing and reaction step. "Metal" in this context does not mean the metal in its metallic form but present in a metal compound, such as the metal component as initially applied or as present in the bulk catalyst composition.

Generally, during the mixing step either at least one metal component is added at least partly in the solid state and at least one metal component is added in the solute state, or all metal components are added at least partly in the solid state, wherein at least one of the metals of the metal components which are added at least partly in the solid state remains at least partly in the solid state during the entire process of the solid route. That a metal component is added "in the solute state" means that the whole amount of this metal component is added as a solution of this metal component in the protic liquid. That a metal component is added "at least partly in the solid state" means that at least part of the metal component is added as solid metal component and, optionally, another part of the metal component is added as a solution of this metal component in the protic liquid. A typical example is a suspension of a metal component in a protic liquid in which the metal is at least partly present as a solid, and optionally partly dissolved in the protic liquid.

To obtain a bulk catalyst composition with high catalytic activity, it is therefore preferred that the metal components, which are at least partly in the solid state during contacting, are porous metal components. It is desired that the total pore volume and pore size distribution of these metal components is approximately the same as those of conventional hydrotreating catalysts. Conventional hydrotreating catalysts generally have a pore volume of 0.05–5 ml/g, preferably of 0.1–4 ml/g, more preferably of 0.1–3 ml/g and most preferably of 0.1–2 ml/g determined by nitrogen adsorption. Pores with a diameter smaller than 1 nm are generally not present in conventional hydrotreating catalysts. Further, conventional hydrotreating catalysts have generally a surface area of at least 10 m²/g and more preferably of at least 50 m²/g and most preferably of at least 100 m²/g, determined via the B.E.T. method. For instance, nickel carbonate can be chosen which has a total pore volume of 0.19–0.39 ml/g and preferably of 0.24–0.35 ml/g determined by nitrogen adsorption and a surface area of 150–400 m$^2$/g and more preferably of 200–370 m$^2$/g determined by the B.E.T. method. Furthermore, these metal components should have a median particle diameter of at least 50 nm, more preferably at least 100 nm, and preferably not more than 5000 μm and more preferably not more than 3000 μm. Even more preferably, the median particle diameter lies in the range of 0.1–50 μm and most preferably in the range of 0.5–50 μm. For instance, by choosing a metal component which is added at least partly in the solid state and which has a large median particle diameter, the other metal components will only react with the outer layer of the large metal component particle. In this case, so-called "core-shell" structured bulk catalyst particles are obtained.

An appropriate morphology and texture of the metal component can either be achieved by applying suitable preformed metal components or by preparing these metal components by the above-described precipitation under such conditions that a suitable morphology and texture is obtained. A proper selection of appropriate precipitation conditions can be made by routine experimentation.

As has been set out above, to retain the morphology and texture of the metal components which are added at least partly in the solid state, it is essential that the metal of the metal component at least partly remains in the solid state during the whole process of this solid route. It is noted again that it is essential that in no case should the amount of solid metals during the process of the solid route becomes zero. The presence of solid metal comprising particles can easily be detected by visual inspection at least if the diameter of the solid particles in which the metals are comprised is larger than the wavelength of visible light. Of course, methods such as quasi-elastic light scattering (QELS) or near forward scattering which are known to the skilled person can also be used to ensure that in no point in time of the process of the solid route, all metals are in the solute state.

The protic liquid to be applied in the solid or solution route of this invention for preparing catalyst can be any protic liquid. Examples include water, carboxylic acids, and alcohols such as methanol or ethanol. Preferably, a liquid comprising water such as mixtures of an alcohol and water and more preferably water is used as protic liquid in this solid route. Also different protic liquids can be applied simultaneously in the solid route. For instance, it is possible to add a suspension of a metal component in ethanol to an aqueous solution of another metal component.

The Group VIB metal generally comprises chromium, molybdenum, tungsten, or mixtures thereof Suitable Group VIII non-noble metals are, e.g., iron, cobalt, nickel, or mixtures thereof Preferably, a combination of metal components comprising nickel, molybdenum and tungsten or nickel, cobalt, molybdenum and tungsten is applied in the process of the solid route. If the protic liquid is water, suitable nickel components which are at least partly in the solid state during contacting comprise water-insoluble nickel components such as nickel carbonate, nickel hydroxide, nickel phosphate, nickel phosphite, nickel formate, nickel sulfide, nickel molybdate, nickel tungstate, nickel oxide, nickel alloys such as nickel-molybdenum alloys, Raney nickel, or mixtures thereof. Suitable molybdenum components, which are at least partly in the solid state during contacting, comprise water-insoluble molybdenum components such as molybdenum (di- and tri) oxide, molybdenum carbide, molybdenum nitride, aluminum molybdate, molybdic acid (e.g. $H_2MoO_4$), molybdenum sulfide, or mixtures thereof. Finally, suitable tungsten components which are at least partly in the solid state during contacting comprise tungsten di- and trioxide, tungsten sulfide ($WS_2$ and $WS_3$), tungsten carbide, tungstic acid (e.g. $H_2WO_4$—$H_2O$, $H_2W_4O_{13}$—$9H_2O$), tungsten nitride, aluminum tungstate (also meta-, or polytungstate) or mixtures thereof These components are generally commercially available or can be prepared by, e.g., precipitation. e.g., nickel carbonate can be prepared from a nickel chloride, sulfate, or nitrate solution by adding an appropriate amount of sodium carbonate. It is generally known to the skilled person to choose the precipitation conditions in such a way as to obtain the desired morphology and texture.

In general, metal components, which mainly contain C, O and/or H beside the metal, are preferred because they are less detrimental to the environment. Nickel carbonate is a preferred metal component to be added at least partly in the solid state because when nickel carbonate is applied, $CO_2$ evolves and positively influences the pH of the reaction mixture. Further, due to the transformation of carbonate into $CO_2$, the carbonate does not end up in the wastewater.

Preferred nickel components which are added in the solute state are water-soluble nickel components, e.g. nickel nitrate, nickel sulfate, nickel acetate, nickel chloride, or mixtures thereof. Preferred molybdenum and tungsten components which are added in the solute state are water-soluble molybdenum and tungsten components such as alkali metal or ammonium molybdate (also peroxo-, di-, tri-, tetra-, hepta-, octa-, or tetradecamolybdate), Mo—P heteropolyanion compounds, Wo-Si heteropolyanion compounds, W—P heteropolyanion compounds, W—Si heteropolyanion compounds, Ni—Mo—W heteropolyanion compounds, Co—Mo—W heteropolyanion compounds, alkali metal or ammonium tungstates (also meta-, para-, hexa-, or polytungstate), or mixtures thereof.

Preferred combinations of metal components are nickel carbonate, tungstic acid and molybdenum oxide. Another preferred combination is nickel carbonate, ammonium dimolybdate and ammonium metatungstate. It is within the scope of the skilled person to select further suitable combinations of metal components. It must be noted that nickel carbonate always comprises a certain amount of hydroxy-groups. It is preferred that the amount of hydroxy-groups present in the nickel carbonate be high.

An alternative method of preparing the catalysts used in the practice of the present invention is to prepare the bulk catalyst composition by a process comprising reacting in a reaction mixture a Group VIII non-noble metal component in solution and a Group VIB metal component in solution to obtain a precipitate. As in the case of the solid route, preferably, one Group VIII non-noble metal component is reacted with two Group VIB metal components. The molar ratio of Group VIB metals to Group VIII non-noble metals applied in the process of the solution route is preferably the same as described for the solid route. Suitable Group VIB and Group VIII non-noble metal components are, e.g. those water-soluble nickel, molybdenum and tungsten components described above for the solid route. Further Group VIII non-noble metal components are, e.g., cobalt or iron components. Further Group VIB metal components are, e.g. chromium components. The metal components can be added to the reaction mixture in solution, suspension or as such. If soluble salts are added as such, they will dissolve in the reaction mixture and subsequently be precipitated. Suitable Group VIB metal salts which are soluble in water are ammonium salts such as ammonium dimolybdate, ammonium tri-, tetra- hepta-, octa-, and tetradecamolybdate, ammonium para-, meta-, hexa-, and polytungstate, alkali metal salts, silicic acid salts of Group VIB metals such as molybdic silicic acid, molybdic silicic tungstic acid, tungstic acid, metatungstic acid, pertungstic acid, heteropolyanion compounds of Mo—P, Mo—Si, W—P, and W—Si. It is also possible to add Group VIB metal-containing compounds which are not in solution at the time of addition, but where solution is effected in the reaction mixture. Examples of these compounds are metal compounds which contain so much crystal water that upon temperature increase they will dissolve in their own metal water. Further, non-soluble metal salts may be added in suspension or as such, and solution is effected in the reaction mixture. Suitable non-soluble metals salts are heteropolyanion compounds of Co—Mo—W (moderately soluble in cold water), heteropolyanion compounds of Ni—Mo—W (moderately soluble in cold water).

The reaction mixture is reacted to obtain a precipitate. Precipitation is effected by adding a Group VIII non-noble metal salt solution at a temperature and pH at which the Group VIII non-noble metal and the Group VIB metal precipitate, adding a compound which complexes the metals and releases the metals for precipitation upon temperature increase or pH change or adding a Group VIB metal salt solution at a temperature and pH at which the Group VIII non-noble metal and Group VIB metal precipitate, changing the temperature, changing the pH, or lowering the amount of the solvent. The precipitate obtained with this process appears to have high catalytic activity. In contrast to the conventional hydroprocessing catalysts, which usually comprise a carrier impregnated with Group VIII non-noble metals and Group VIB metals, said precipitate can be used without a support. Unsupported catalyst compositions are usually referred to as bulk catalysts. Changing the pH can be done by adding base or acid to the reaction mixture, or adding compounds, which decompose upon temperature, increase into hydroxide ions or $H_+$ ions that respectively increase or decrease the pH. Examples of compounds that decompose upon temperature increase and thereby increase or decrease the pH are urea, nitrites, ammonium cyanate, ammonium hydroxide, and ammonium carbonate.

In an illustrative process according to the solution route, solutions of ammonium salts of a Group VIB metal are made and a solution of a Group VIII non-noble metal nitrate is made. Both solutions are heated to a temperature of approximately 90° C. Ammonium hydroxide is added to the Group VIB metal solution. The Group VIII non-noble metal solution is added to the Group VIB metal solution and direct precipitation of the Group VIB and Group VIII non-noble metal components occurs. This process can also be conducted at lower temperature and/or decreased pressure or higher temperature and/or increased pressure.

In another illustrative process according to the solution route, a Group VIB metal salt, a Group VIII metal salt, and ammonium hydroxide are mixed in solution together and heated so that ammonia is driven off and the pH is lowered to a pH at which precipitation occurs. For instance when nickel, molybdenum, and tungsten components are applied, precipitation typically occurs at a pH below 7.

Independently from whether the solid or solution route is chosen the resulting bulk catalyst composition preferably comprises and more preferably consists essentially of bulk catalyst particles having the characteristics of the bulk catalyst particles described above.

The bulk catalyst composition can generally be directly shaped into hydroprocessing particles. If the amount of liquid of the bulk catalyst composition is so high that it cannot be directly subjected to a shaping step, a solid liquid separation can be performed before shaping. Optionally the bulk catalyst composition, either as such or after solid liquid separation, can be calcined before shaping.

The median diameter of the bulk catalyst particles is at least 50 nm, more preferably at least 100 nm, and preferably not more than 5000 $\mu$m and more preferably not more than 3000 $\mu$m. Even more preferably, the median particle diameter lies in the range of 0.1–50 $\mu$m and most preferably in the range of 0.5–50 $\mu$m.

If a binder material is used in the preparation of the catalyst composition it can be any material that is conventionally applied as a binder in hydroprocessing catalysts. Examples include silica, silica-alumina, such as conventional silica-alumina, silica-coated alumina and alumina-coated silica, alumina such as (pseudo)boehmite, or gibbsite, titania, zirconia, cationic clays or anionic clays such as saponite, bentonite, kaoline, sepiolite or hydrotalcite, or mixtures thereof. Preferred binders are silica, silica-alumina, alumina, titanic, zirconia, or mixtures thereof. These binders may be applied as such or after peptization. It is also possible to apply precursors of these binders that, during the process of the invention are converted into any of the above-described binders. Suitable precursors are, e g., alkali metal aluminates (to obtain an alumina binder), water glass (to obtain a silica binder), a mixture of alkali metal aluminates and water glass (to obtain a silica alumina binder), a mixture of sources of a di-, tri-, and/or tetravalent metal such as a mixture of water-soluble salts of magnesium, aluminum and/or silicon (to prepare a cationic clay and/or anionic clay), chlorohydrol, aluminum sulfate, or mixtures thereof.

If desired, the binder material may be composited with a Group VIB metal and/or a Group VIII non-noble metal, prior to being composited with the bulk catalyst composition and/or prior to being added during the preparation thereof. Compositing the binder material with any of these metals may be carried out by impregnation of the solid binder with these materials. The person skilled in the art knows suitable impregnation techniques. If the binder is peptized, it is also possible to carry out the peptization in the presence of Group VIB and/or Group VIII non-noble metal components.

If alumina is applied as binder, the surface area preferably lies in the range of 100–400 $m^2/g$, and more preferably 150–350 $m^2/g$, measured by the B.E.T. method. The pore volume of the alumina is preferably in the range of 0.5–1.5 ml/g measured by nitrogen adsorption.

Generally, the binder material to be added in the process of the invention has less catalytic activity than the bulk catalyst composition or no catalytic activity at all. Consequently, by adding a binder material, the activity of the bulk catalyst composition may be reduced. Therefore, the amount of binder material to be added in the process of the invention generally depends on the desired activity of the final catalyst composition. Binder amounts from 0–95 wt. % of the total composition can be suitable, depending on the envisaged catalytic application. However, to take advantage of the resulting unusual high activity of the composition of the present invention, binder amounts to be added are generally in the range of 0.5–75 wt. % of the total composition.

The catalysts of this invention are typically activated by a sulfiding agent in the presence of hydrogen. The sulfur compounds that can be used include $H_2S$, carbon disulfide, methyldisulfide, ethyldisulfide, propyldisulfide, isopropyldisulfide, butyldisulfide, tertiary butyldisulfide, thianaphthene, thiophene, secondary dibutyldisulfide, thiols, sulfur containing hydrocarbon oils and sulfides such as methylsulfide, ethylsulfide, propylsulfide, isopropylsulfide, butylsulfide, secondary dibutylsulfide, tertiary butylsulfide, dithiols and sulfur-bearing gas oils. Any other organic sulfur source that can be converted to $H_2S$ over the catalyst in the presence of hydrogen can be used. The catalyst may also be activated by an organo sulfur process as described in U.S. Pat. No. 4,530,917 and other processes described therein and this description is incorporated by reference into this specification.

Generic hydrogenation treating conditions include reactions in the temperature of about 100° C.–350° C. and pressures of between five atmospheres (506 kPa) and 300 atm. (30390 kPa) hydrogen, for example, 10 to 275 atm. (1013 kPa to 27579 kPa). In one embodiment the temperature is in the range including 180° C. and 320° C. and the pressure is in the range including 15195 kPa and 20260 kPa hydrogen. The hydrogen to feed volume ratio to the reactor under standard conditions (25° C., 1 atoms. pressure) typically can range from 20–200, for water-white resins 100–200 is preferred.

Catalyst activity decreases over time due to carbonaceous deposition onto the catalyst support, this can be eliminated or removed by regenerating the catalyst bed with high pressure hydrogen at temperatures between about 310° C.–350° C. High pressure here means, for example, at least about 180 bar. This regeneration is best accomplished in the absence of hydrocarbon feed to the reactor, e.g., during interruption of the hydrogenation process.

Hydrogenated polymeric resins of the invention specifically include hydrocarbon resins suitable as tackifiers for adhesive compositions, particularly adhesive compositions comprising polymeric base polymer systems of either natural or synthetic elastomers, including such synthetic elastomers as those from styrene block copolymers, olefinic rubbers, olefin derived elastomers or plastomers, and various copolymers having elastomeric characteristics, e.g., ethylene-vinyl ester copolymers. Such adhesive compositions find particular utility in hot melt adhesive and pressure sensitive adhesive applications such as those for adhesive tapes, diaper tabs, envelopes, note pads, and the like. Often compatibility of the tackifier with polymeric base polymer systems is best achieved by selection of a hydrocarbon resin that is high in aromatic monomer content. Concurrently it is sought to select a tackifier that has color characteristics commensurate with those of the base polymer system, preferably both the polymer system and its tackifier will be essentially transparent and low in chromophores, that is, color. Retention of this low color characteristic is important during heating operations such as those present in formulation by melt processing and application of the adhesive compositions to substrate materials under elevated temperatures. Adequate hydrogenation is known to achieve desirable heat stability of low color properties in polymeric hydrocarbon resins made from either aliphatic or aromatic monomers, or mixes thereof. Both objectives can be achieved by use of the process of the present invention.

The following examples are presented to illustrate the foregoing discussion. All parts, proportions and percentages are by weight unless otherwise indicated. Although the examples may be directed to certain embodiments of the present invention, they are not to be viewed as limiting the invention in any specific respect.

EXAMPLES

Tests were conducted to demonstrate the utility of the catalyst of the present invention in a resin hydrogenation process. An aromatic-modified $C_5/C_9$ aliphatic resin, commercially available as Escorez 2101™ from ExxonMobil Chemical Company, was hydrogenated in a fixed-bed reactor. Escorez 2101™ contains about 150 ppm chlorides. The fixed bed reactor was operated at 3000 psig $H_2$ pressure, with 1 liquid vol/bed vol/hr and 150 gas-to-liquid vol ratio. Two catalysts were tested. Catalyst A is an unsupported Ni/Mo/W catalyst prepared according to the present invention. Catalyst B is an alumina-supported Ni/W catalyst that is typical of current hydrogenation catalysts. Similar catalysts are disclosed in more detail in U.S. Pat. No. 5,820,749.

TABLE I

Hydrogenation of ESCOREZ 2101 ™ Hydrocarbon Resin

| Run number | Catalyst | Temp (C.) | Color (YI) | Softening point (C.) | Percent Aromaticity |
|---|---|---|---|---|---|
| Unhydrogenated resin | | | 70.4 | 91.1 | 18.65 |
| 1 | A | 202 | 19.4 | 94.4 | 17.34 |
| 2 | A | 237 | 3.13 | 77.2 | 15.76 |
| 3 | A | 238 | 2.79 | 75 | 15.79 |
| 4 | A | 238 | 2.72 | 74.3 | 15.83 |
| 5 | B | 215–231 | 10.3 | 87.1 | 17.25 |
| 6 | B | 215–231 | 16.2 | 88.4 | |

The data in Table I shows that the unsupported catalyst of the present invention is very efficient in removing color (i.e. hydrogenating the conjugated double bonds) in the resin. Furthermore, like the alumina-supported catalyst, it retains most of the resin's aromaticity.

The unsupported catalyst of the present invention can perform equally well in hydrogenating non-chlorinated resins such as dicyclopentadiene-based resins produced by thermal polymerization. Therefore, the catalyst lends itself well to applications where one fixed-bed hydrogenator supports resin feed from both thermal and chloride-catalyst polymerization units.

While certain representative embodiments and details have been shown for the purposes of illustrating the invention, it will be apparent to those skilled in the art that various changes in the process and products disclosed herein may be made without departing from the scope of the invention, which is defined in the appended claims.

What is claimed is:

1. A hydrotreating process for hydrocarbon resin or rosin molecules comprising contacting said molecules with hydrogen in the presence of a bulk multimetallic hydrogenation catalyst comprised of at least one Group VIII non-noble metal and at least two Group VIE metals and wherein the molar ratio of Group VIB metal to Group VIII non-noble metal is from about 10:1 to about 1:10.

2. The hydrotreating process of claim 1 comprising hydrotreating at a temperature of 100° C. to 330° C. and hydrogen pressure of 1013 kPa to $27.6 \times 10^2$ kPa.

3. The process of claim 2 wherein said temperature is at least 180° C. and said pressure is 1013 kPa to $15.2 \times 10^3$ kPa.

4. The process of claim 1 wherein said hydrocarbon molecules comprise petroleum resins.

5. The process of claim 1 wherein said hydrocarbon molecules comprise aliphatic or cycloaliphatic petroleum resins.

6. The process of claim 1 wherein said hydrocarbon molecules comprise aliphatic-aromatic petroleum results.

7. The process of claim 1 wherein said hydrocarbon resin is a natural resin or esterified rosin.

8. The process of claim 1 wherein said hydrocarbon resin has been prepared by Friedl-Crafts polymerization with a Lewis acid polymerization catalyst.

9. The process of claim 8 wherein said Lewis acid polymerization catalyst is $AlCl_3$.

10. A hydrotreating process for hydrocarbon resin or rosin molecules consisting essentially of contacting of contacting said molecules with hydrogen in the presence of an unsupported bulk multimetallic hydrogenation catalyst comprised of at least one Group VIII non-noble metal and at least two Group VIB metals and wherein the molar ratio of Group VIB metal to Group VIII non-noble metal is from about 10:1 to about 1:10.

11. The hydrotreating process of claim 10 wherein the hydrotreating occurs at a temperature of 100° C. to 330° C. and a hydrogen pressure of 1013 kPa to $27.6 \times 10^3$ kPa.

12. The hydrotreating process of claim 11 wherein said temperature is at least 180° C and said pressure is 1013 kPa to $15.2 \times 10^3$ kPa.

13. The hydrotreating process of claim 10 wherein said hydrocarbon molecules comprise petroleum resins.

14. The hydrotreating process of claim 10 wherein said hydrocarbon molecules comprise aliphatic or cycloaliphatic petroleum resins.

15. The hydrotreating process of claim 10 wherein said hydrocarbon molecules comprise aliphatic-aromatic petroleum resins.

16. The hydrotreating process of claim 10 wherein said hydrocarbon resin is a natural resin or esterified rosin.

17. The hydrotreating process of claim 10 wherein said hydrocarbon resin has been prepared by Fridl-Crafts polymerization with a Lewis acid polymerization catalyst.

18. The hydrotreating process of claim 17 wherein said Lewis acid polymerization catalyst is $AlCl^3$.

* * * * *